United States Patent [19]

Amatore et al.

[11] Patent Number: 5,296,105
[45] Date of Patent: Mar. 22, 1994

[54] PROCESS USING TRANSITION METAL COMPLEXES FOR THE SEPARATION OF DIOXYGEN FROM A GAS MIXTURE BY ELECTRODECOMPLEXATION

[75] Inventors: Christian Amatore, Paris; Saïd Aziz, Le Mee sur Seine; Anny Jutand, Paris; Francois Draskovic, Fontenay-le-Fleury, all of France; Kenneth Yamaguchi, Laguna Beach, Calif.; Panayotis Cocolios, Limours, France

[73] Assignee: L'Air Liquide, Societe Anonyme pour L'Etude et l'Exploitation des Procedes Georges Claude, Paris, France

[21] Appl. No.: 777,213

[22] PCT Filed: Mar. 19, 1991

[86] PCT No.: PCT/FR91/00218

§ 371 Date: Nov. 6, 1991

§ 102(e) Date: Nov. 6, 1991

[87] PCT Pub. No.: WO91/14649

PCT Pub. Date: Oct. 3, 1991

[30] Foreign Application Priority Data

Mar. 27, 1990 [FR] France .................................. 90 03886

[51] Int. Cl.⁵ .............................................. C25B 1/02
[52] U.S. Cl. ................................ 204/59 R; 95/138
[58] Field of Search .............. 204/59 R, 129; 55/2; 556/21, 22, 23, 19, 13, 12; 568/8

[56] References Cited

U.S. PATENT DOCUMENTS

| | | | |
|---|---|---|---|
| 4,457,898 | 7/1984 | Hill et al. | 423/219 |
| 4,475,994 | 10/1984 | Gagne et al. | 204/129 |
| 4,680,037 | 7/1987 | Ramprasad et al. | 55/16 |
| 4,952,289 | 8/1990 | Ciccone et al. | 204/235 |

FOREIGN PATENT DOCUMENTS 8802036 3/1988 World Int. Prop. O. .

*Primary Examiner*—Kathryn Gorgos
*Attorney, Agent, or Firm*—Oblon, Spivak, McClelland, Maier & Neustadt

[57] ABSTRACT

A process for separating dioxygen from a gaseous mixture containing dioxygen, which entails:

a) absorbing dioxygen by one or more transition metal complexes at a low oxidation state of the formula (A):

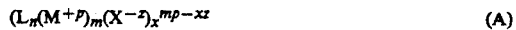

(A)

the absorption causing formation of a peroxo dihapto deoxygenated product complex of the formula (B):

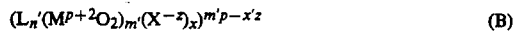

(B)

b) desorbing oxygen from the complex by electrochemically oxidizing the peroxo dihapto product complex obtained by reaction of the complex of the formula (A) wiht O₂: and c) recovering the absorbed oxygen.

35 Claims, 4 Drawing Sheets

PROCESS USING TRANSITION METAL COMPLEXES FOR THE SEPARATION OF DIOXYGEN FROM A GAS MIXTURE BY ELECTRODECOMPLEXATION

BACKGROUND OF THE INVENTION

1. Field of the Invention

This invention relates to the use of transition metal complexes for the separation of dioxygen from a gas mixture containing dioxygen. Numerous transition metal complexes of the $C_yM$ type where the transition metal M is bound to y molecules of organic complexing species C, are capable of binding the molecular oxygen.

2. Description of the Background

The resulting dioxygen complexes are either of the superoxo type: $C_yM$—O—O, or $\mu$-peroxo: $C_yM$—O—O—$MC_y$, peroxo dihapto:

hydroperoxo: $C_yM$—O—OH, oxo: $C_yM$=O, or 82 oxo: $C_yM$—O—$MC_y$. Among these structures, only the first three correspond to a bonding of the $O_2$ molecule to the metal without cleavage of the molecule and, thus, are considered as candidates for the separation of the molecular oxygen from a gas mixture. The most commonly used complexes are complexes of cobalt with a Schiff base, an aminoacids, a porphyrin, a polyalkylamine or a polyalkylaminoacid, or complexes of iron with a cryptand or a porphyrin. Other complexes are also used which are complexes of transition metals such as manganese or copper, coordinated respectively with one or with several phosphines or with a protein.

The binding of dioxygen to these complexes leads to species of the superoxo or $\mu$-peroxo type, and is reversible; the desorption step being effected by increasing of the temperature and decreasing the gas partial pressure. However, in order to increase the dioxygen separation efficiency by using such complexes, it is necessary to run the process in a continuous manner with complexes that present a very high affinity for the dioxygen. This is unfortunately realize when the metal-oxygen bond is strong and requires a high energy level for breakage in the desorption step. The U.S. Pat. No. 4,475,994 of MAXDEM Inc. suggests a way to overcome this problem which is the use of a solution of a cobalt complex capable of dioxygen binding when contacted with a gas mixture and the use of an electrochemical device for the desorption of dioxygen. The metal complex used in this process binds the dioxygen in a suspension arrangement $C_yCo$—O—O or a $\mu$-peroxo $C_yCo$—O—O—$CoC_y$ arrangement when the cobalt is originally at a +II oxidation state. With an appropriate ligand, it is possible to electrochemically oxidize the complex without changing the organic ligand and, thus, generate gaseous dioxygen at the anode of an electrochemical cell.

This oxidation reaction leads to the formation of a Co(III) complex which is inactive towards $O_2$ and which is reduced in the cathode compartment of the same cell to generate a Co(II) species capable of $O_2$ binding. An example of such a cycle is shown on Scheme I where the dioxygen is bound in a superoxo manner:

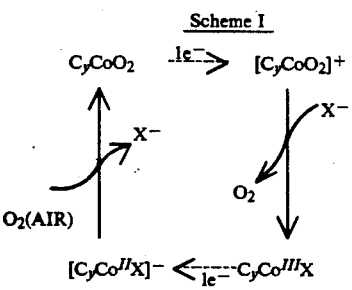

Scheme I

The cobalt complexes of the superoxo type, usually soluble in organic media, or of the $\mu$-peroxo type, usually soluble in aqueous media, which is known for their capacity to bind, carry and unload the molecular oxygen according to the electrochemical cycle shown in Scheme I, present rather limited lifetime. The understanding of the reaction pathway and the analysis of the complex molecule degradation in the presence of dioxygen under electrochemical treatment, are rather difficult, especially in aqueous media where numerous equilibria have to be considered.

Among these equilibria, a person skilled in the art will mention the ones between protonated and unprotonated ligands (pH dependant), between the ligand and the metal (ligand basicity dependant), between species that require different coordinate environment (tetra coordinated complex$\rightleftarrows$pentacoordinated complex$\rightleftarrows$hexacoordinated complex), the spin equilibria such as low spin $Co^{II}\rightleftarrows$high spin $Co^{II}$ (ligand field dependant), the dioxygen complexation equilibrium and the dimerisation of the oxygenated complex. If the chemical reactions and/or the electrochemical reactions are not or they are badly controlled, the organic ligand as well as the metal ion may be altered, leading to an irreversible degradation of the complex.

SUMMARY OF THE INVENTION

In order to have dioxygen complexes that satisfy the requirements of the technique for the separation of the dioxygen from a gaseous mixture, the inventors have used a new family of transition metal complexes which exhibit a simplified coordination scheme and a limited number of reactions in solution, which are formed by use of simple, commercially available organic ligands, and that follow an electrochemical cycle similar to the one described in scheme I.

DESCRIPTION OF THE INVENTION

This process for the separation of dioxygen from a gas mixture may be described as follows:
the absorption dioxygen by low oxidation state transition metal complexes of the general formula (A):

$$[L_n(M^{+p})_m(X^{-s})_x]^{mp-xs} \tag{A}$$

in which:
L represents a coordination site which is a part of one or several ligands, inorganic or organic, mono- or polydentate, identical or different, the said ligands being capable of stabilizing low valences of M, chosen especially among the following ligands:
carbon monoxide
phosphines
phosphine oxides
phospites aliphatic or aromatic amines
amides
carboxylic acids
aliphatic or aromatic thiols
sulfoxides
nitriles
isocyanates
arsines
alkyl (aryl) silanes or alkyl (aryl) siloxanes
heterocycles containing nitrogen, phosphorus, oxygen or sulfur atoms, saturated or unsaturated, M is a transition metal capable of binding $O_2$ leading to peroxo dihapto, dioxygenated species,

chosen especially among Pd, Pt, Rh, Ni, Ir and Mo.

X is an organic anion, capable of coordination, such as, for example, the carboxylate ion, or an inorganic anion such as, for example, an halide, and more specifically a chloride ion.

n, integer ranging from 2 to 12, represents the number of coordination sites L, p represents the oxidation state number of M in the complex of formula (A), m, equal to 1 or 2, represents the number of metal centers of the complex, z, integer ranging from 1 to 3, represents the charge of the $X^{-s}$ anion, x, ranging from 0 to 4, represents the number of anions X, identical or different, coordinated to the metal center(s) M.

the absorption leading to a peroxo dihapto dioxygenated complex of formula (B):

$$[L_{n'}(M^{p+2}O_2)_{m'}(X^{-z})_{x'}]^{m'p-x'z} \quad (B)$$

in which:

L, M, X, p, z have the same meanings as above, n', m', x' have respectively the same meanings than n, m, x with $2 \leq n' \leq n$, $1 \leq m' \leq m$, $0 \leq x' \leq x$.

the desorption of dioxygen by electrochemical oxidation of the peroxo dihapto product (B) obtained by reaction of the complex of formula (A) with $O_2$, the recovery of the unloaded dioxygen, and if desired, for a continuous process:

the electrochemical reduction of the complex resulting from the electrooxidation step of compound (B), leading to a regenerated complex (A).

A group of metal complexes that can be used in this invention are represented by formula (C), $[L_nM^{+p}]^{+p}$, where L, M, n and p have the same meanings as above.

In an other group of complexes of this invention, the metal M is not only coordinated to ligands that possess coordination sites L, but also to anions in order to occupy all or at least a part of the vacant coordination sites of M.

This group is represented by formula (D):

$$[L_n(M^{+p})(X^{-s})_x]^{p-xz} \quad (D)$$

Where L, M, X, n, p, x and z are as defined above.

This invention also relates to dinuclear complexes of formula (E):

$$[L_n(M^{+p})_2(X^{-z})_x]^{2p-xs} \quad (E)$$

where L, M, X, n, p, z and x are as defined above and where the dinuclear structure is maintained either with bridging anions $X^{-s}$ or with polydentate ligands that possess at least two coordination sites L, or with a metal-metal bond, or with a combination of these bindings.

In the above formula (A) to (E), the metal complexes that are usable in this invention may be anions or cations. They are then associated to one or several non coordinative counterions, organic or inorganic, that couterbalance their charge. These ions come from the supporting electrolyte and may be quaternary ammonium salts, quaternary phosphonium salts, alkaline or alkaline-earth metals complexed or not or analogs for the cations, and halide, tetrafluoroborate, hexafluorophosphate, sulfate, carbonate, phosphate ions, or analogs, for the anions.

The dioxygenated complexes of formula (B) result from the binding of dioxygen by compounds of formula (A) and more specifically by compounds of formula (C), (D) or (E). The compounds (A), (C), (D) and (E) can be synthesized before use or may be prepared "in situ", starting from commercially available compounds, or not.

Metal salts of various oxidation states may serve as precursors of the active species, such as halide salts, acetates, nitrates, sulfates, fluoroborates, perchlorates, or analogs.

Compounds that are especially well adapted for the process when M is Pd, are $PdCl_2$ and $Na_2PdCl_4$.

Ligands that are especially appropriate for the preparation of complexes of this invention are chosen among the phosphines, such as the triphenylphosphines, the alkyl-, aryl- or alkylarylphosphines, mono- or bidentates, and more particularly the triphenylphosphine and the tri-n-butylphosphine. In order to get water soluble ligands, compounds that possess a hydrophile function on one of the substituants of the phosphorus will be preferred, such as sulfonated phosphines like the trisulfonated triphenyl phosphine $P(C_6H_4SO_3H)_3$ or the disulfonated one $P(C_6H_5)(C_6H_4SO_3H)_2$ or the monosulfonated one $P(C_6H_5)_2(C_6H_4-SO_3H)$. Phosphine oxides and phosphites are also convenient in aqueous media. Metal complexes that are especially preferred in this invention, are formed with a transition metal M that is palladium, platinum nickel or rhodium. The electrochemical oxidation step is carried out in the anodic compartment of an electrolysis cell. Appropriate electrolytes are of the type of perfluoroborate or tetraphenylborate, or perfluorophosphate or halide or sulfate or carbonate on phosphate of alkalin or alkalinearth metal, complexed or not, of quaternary ammonium salt, of phosphonium salt and could be, as examples, tetra-n-butylammonium tetrafluoroborate of triethylbenzylammonium hexafluorophosphate.

The applied potential is chosen in consideration of the oxygenated metal complex to be oxidized and of the bulk medium composition.

The oxidation step is followed by the desorption of dioxygen which also occurs in the anodic compartment of the electrolysis cell, the separation of dioxygen from the solution being carried out in a gas-liquid separation tower located after the anodic compartment.

For a continuous operation of the dioxygen separation process, from the outlet of the separation tower, the solution is introduced in the cathodic compartment of the electrolysis cell where an electrochemical reduction is carried out at a more negative potential than the one used in the oxidation step, leading to a complex of lower valence, capable of binding again the dioxygen in an absorption tower located between the outlet of the cathodic compartment and the inlet of the anodic compartment, where the electrochemical oxidation-reduction cycle is resumed. The above-mentioned electrochemical oxidation-reduction cycle is represented on schemes IIa, IIb, IIc, IId where L, M, X, p, z, n, m, x, n', m', x' have the same meanings as above and n", m", x" have the same meanings than n', m' and x' respectively:

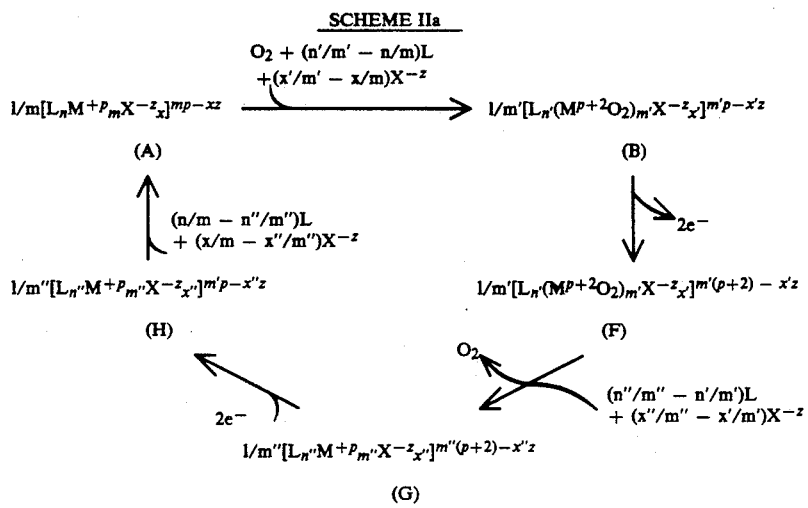

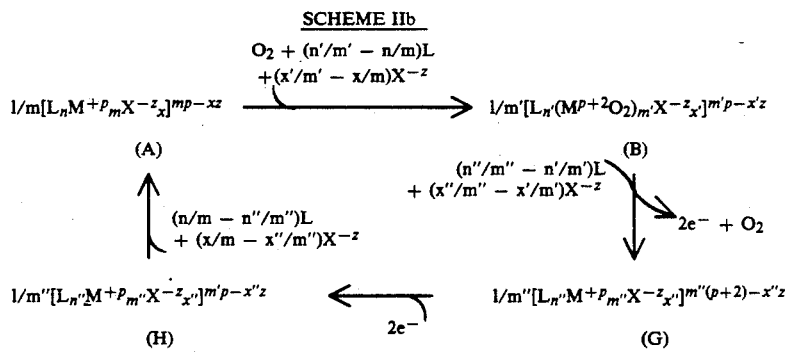

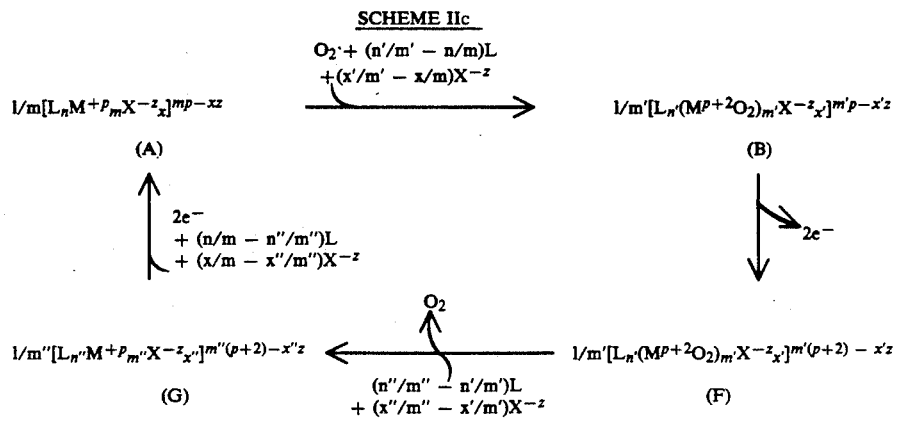

SCHEME IId

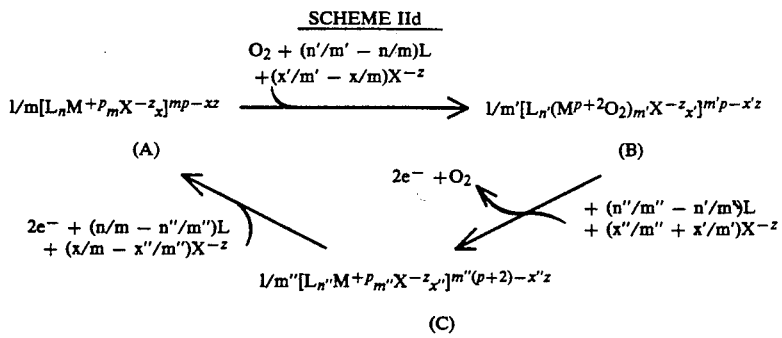

Since the intermediate species (F) and (H) are very short-lived to be accurately characterized, the four schemes IIa, IIb, IIc, and IId are equally possible. In the same manner, (G) may represent several intermediate species resulting from ligand exchanges during the cycle. According to one aspect of this invention, the dioxygen absorption step takes place by contacting the gas mixture with the reduced form of the metal complex in solution.

According to another aspect of this invention, the active species (A) is generated in situ: a mixture of a metal halide such as $PdCl_2$ or $Na_2PdCl_4$, and a ligand such as the triphenylphosphine or the tri-n-butylphosphine is introduced in the cathodic compartment, leading quickly to a species (G) (in the above example $(R_3P)_2PdCl_2$ with R=phenyl or n-butyl). The active species (A) is obtained by reduction of the species (G) at an appropriate potential value and the cycle is then performed as described above.

When the species (G) is reducible at a potential close or more negative than the reduction potential of dioxygen into the superoxyde ion, an advantageous aspect of this process is the reaction of the generated superoxyde ion in the cathodic compartment with the species (G) to lead directly to the dioxygenated complex (B). As an example, if (G) is the complex $(R_3P)_2PdCl_2$, the reaction may be written as follows:

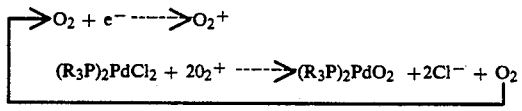

Such a transformation may be advantageously performed in an electrochemical cell under pressure or with a porous cathode for gas-diffusion. The porous cathode also presents the following two advantages:
compared to the classical aspect of this invention, the absorption tower is not required anymore,
compared to the use of a pressurized cell, the saturation of the solution with the other components of the gas mixture containing dioxygen, is avoided.

In an other aspect of this process, the complex solution is made with an organic solvent. In that respect, a solvent of flow ohmic drop will be preferred. Appropriate solvents of that kind will be the dimethyl formamide, the dimethyl sulfoxide acetonitrile or else benzonitrile, dichloromethane, tetrahydrofuran.

According to another aspect of this invention, the process will be performed in an aqueous medium, the ligands used being chosen among water-soluble ligands.

According to this invention, the separation of dioxygen is performed under atmospheric pressure.

In another aspect of this invention, a high pressure of 1 to 100 bar and preferably from 1 to 20 bar may be used. The complex solution could then be contacted with compressed air, or in an other mode, the absorption could be performed at atmospheric pressure and the ligand is then compressed with a pump up to the desired pressure.

This process allows the separation of dioxygen in a continuous manner.

It also allows the separation of dioxygen from a gas mixture to be purified, and is more particularly interesting for the purification of gases such as $N_2$, Ar or $CO_3$.

This invention will be illustrated in the following with examples related to the oxydo-reduction studies of complexes used according to this invention.

BRIEF DESCRIPTION OF THE DRAWINGS

More specifically.

FIG. 1 relates to the electrochemistry of the complex $L_4PD^0$ where L represents the triphenylphosphine. The curve 1A is the voltammogram of the complex $(PPh_3)_4PD^0$ under argon atmosphere; the curve 1B is the one of the same complex after introduction of dioxygen; the curve 1C is the voltammogram of $(PPh_3)_4PD^0$ in the presence of an excess of $O_2$, and the curve 1D is the one resulting from an addition of 2 equivalents vs the starting complex of $nBu_4N^+Cl^{-1}$ in the solution of 1C.

FIGS. 2 and 3 are voltammograms of the complex $(PPh_3)_2PdO_2$ prepared by chemical means and dissolved in dimethylformamide. More specifically, the FIG. 2 represents the voltammograms recorded in an initial cathodic scan for the complex $(PPh_3)_2PdO_2$ alone (curve 2A) and after addition of 2 equivalents of $nBu_4N^+Cl^-$ (curve 2B).

FIG. 3 represents the voltammograms recorded in an initial anodic scan, for $(PPh_3)_2PdO_2$ alone (curve 3A), and after addition of 2 equivalents of $nBu,N^+Cl^-$ (curve 3B).

FIG. 4 represents the voltammograms recorded for the complex $(PPh_3)_2PdO_2$ prepared in situ in dimethylformamide starting from $PdCl_2$ and $PPh_3$. More specifically, curves 4A to 4D represent:
the complex $(PPh_3)_2PdCl_2$ alone (curve 4A)
the complex $(PPh_3)_2PdCl_2$ under low $O_2$ partial pressure (curve 4B).
the complex $(PPh_3)_2PdCl_2$ under air (curve 4C)
the complex $(PPh_3)_2PdCl_2$ under pure $O_2$ atmosphere (curve 4D).

EXAMPLE 1

Electrochemical Study of the Metal Complex $L_4Pd^0$ in Which the Metal is Coordinated to Four Monodentate Triphenylphosphine $PPh_3$ Ligands The study of the oxydo-reduction potentials has been performed in dimethylformamide (DMF) or dichloromethane ($CH_2Cl_2$) in the presence of 0.3M tetra-n-butylammonium tetrafluoroborate ($nBu_4NBF_4$) as supporting electrolyte. The concentration of $L_4Pd^0$ is 2 mM.

The potentials have been recorded versus a Saturated Calomel Electrode (SCE) by cyclic voltammetry on gold electrode (Au) or carbone (C) electrode with a scan rate of 200 and 100 mV/s respectively.

A. Electrochemistry of $L_4Pd^0$ in the Absence of Dioxygen

Oxidation: $L_4Pd^0 \rightarrow [L_2Pd^{II}]^{2+} + 2e^- + 2L$ $E_{ox}$ = +0.13 V (DMF, Au)
 = +0.07 V (DMF, C)
$E_{\frac{1}{2}}$ = +0.02 V ($CH_2Cl_2$, C, reversible).

$E_{red}$ = -1.68 V (DMF, Au)
 = -1.62 V (DMF, C)
 = -1.73 V ($CH_2Cl_2$, Au)
 = -1.74 V ($CH_2Cl_2$, C)

The reduced species is capable of binding dioxygen again and is oxidized in the same manner as the one described above, with 2 electrons, around +0.50 V.

This species has more affinity towards dioxygen then its precursor $L_4Pd^0$.

Figure 1:
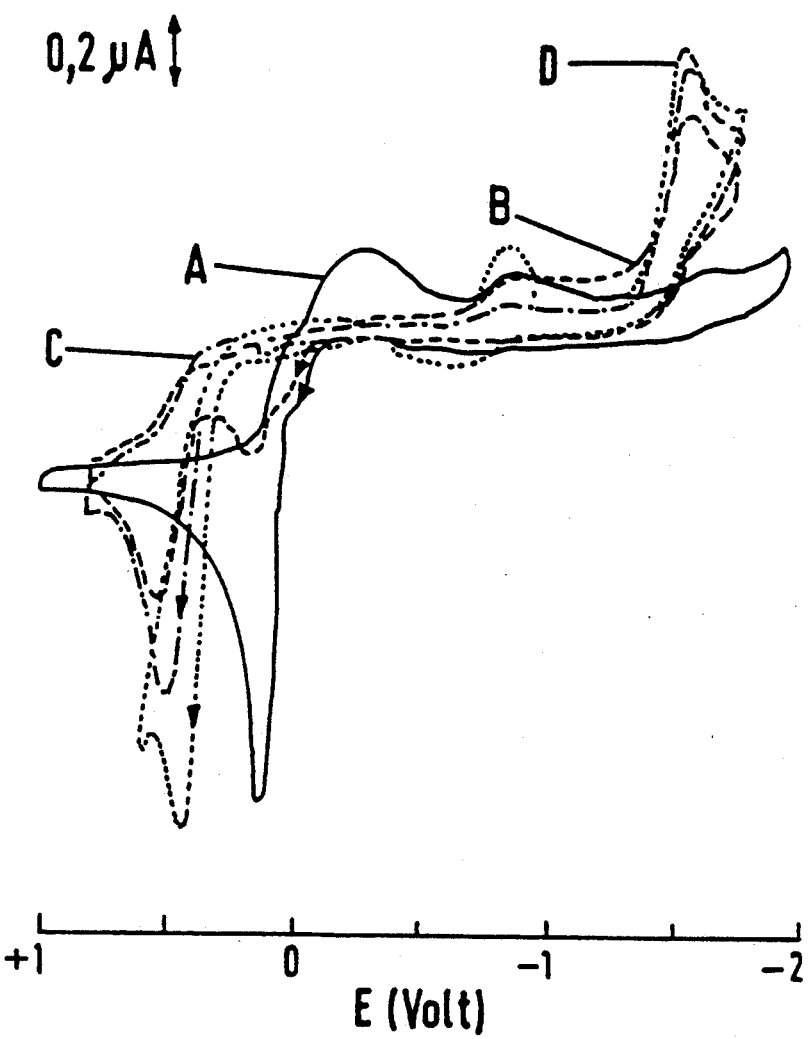
FIGS. 1 to 4 represent voltammograms of selected examples.

These redox reactions are illustrated on FIG. 1 where are represented the cyclic voltammograms, recorded in DMF, of the complexes:
$(PPh_3)_4Pd^0$ under argon atmosphere (FIG. 1A)
$(PPh_3)_4Pd^0$ under dioxygen atmosphere (FIGS. 1B and 1C).

Figure 2:
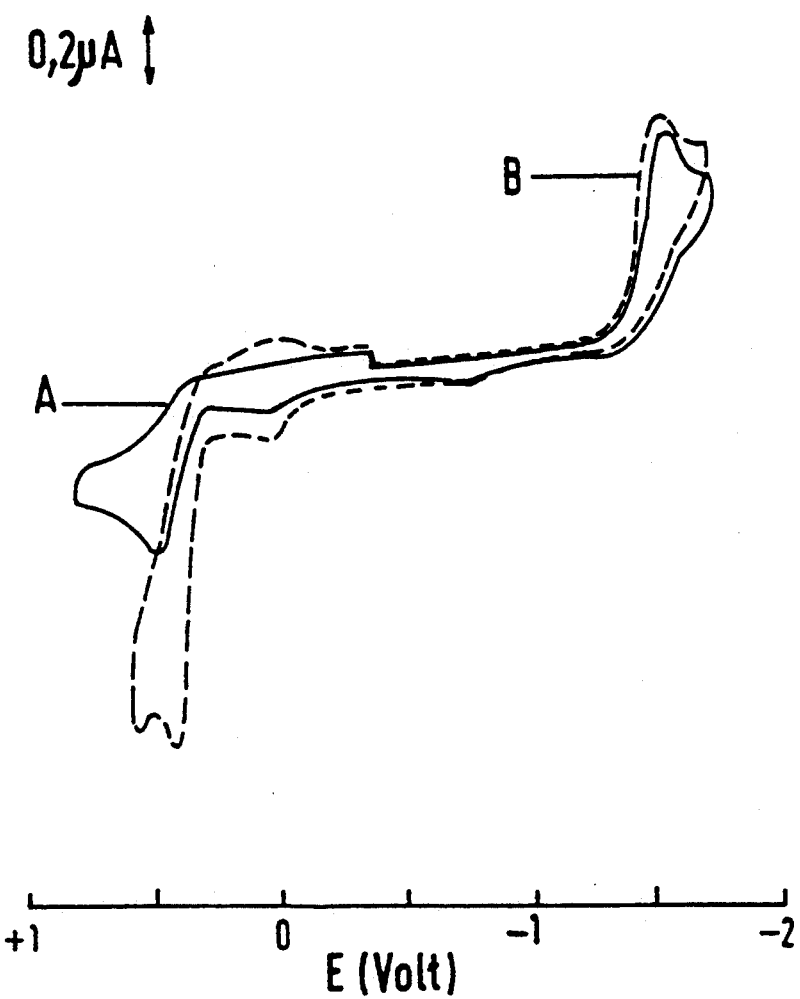

The redox reactions are also attributed by the study of the redox behavior of the complex $(PPh_3)PdO_2$, under the same conditions, as illustrated on FIG. 2 (curves 2A and 2B).

all the above observations are consistent, for the complex $L_4Pd^0$, with the following scheme (Scheme III).

SCHEME III

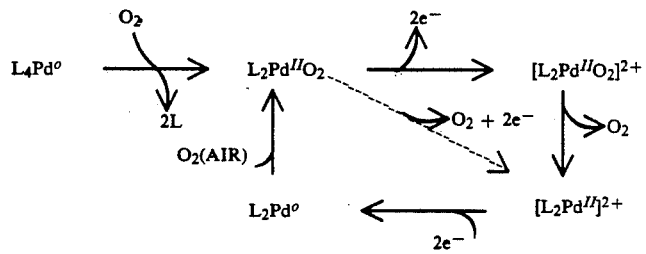

B. Electrochemistry of $L_4Pd^0$ in the Presence of Dioxygen

In the presence of a gas mixture containing dioxygen, such as air, the complex $L_4Pd^0$ leads to a dioxygenated complex $L_2Pd^{II}O_2$ according to:

Oxidation:
$L_4Pd^0 + O_2 \rightarrow L_2Pd^{II}O_2 + 2L$
$L_2Pd^{II}O_2 \rightarrow [L_2Pd^{II}]^{2+} + O_2 + 2e^-$ $E_{ox}$ = +0.52 V (DMF, Au)
 = +0.48 V (DMF, C)
 = +0.64 V ($CH_2Cl_2$, Au)
 = +0.59 V ($CH_2Cl_2$, C)

The oxidation of the complex $L_2Pd^{II}O_2$ is irreversible at potentials close to +0.50 V (vs SCE). The chemical reaction is followed by a visible gas evolution in the case of an electrolysis at controlled potential (+0.60 V).

Reduction:

$L_2Pd^{II}O_2 + 2e^- \rightarrow [L_2Pd^q]^{+1} + O_2^{-(2-q)}$ where q=0 or 1.

EXAMPLE 2

Electrochemistry of $L_4Pd^0$ in the Presence of Dioxygen and Chloride Ions. Redox Potentials of Chlorinated Solutions of $L_4PD^0$ In the presence of chloride ions new, more stable, complexes are formed:

$L_2Pd^{II}O_2 + xCl^- \rightarrow [L_2Pd^{II}O_2Cl_x]^{-x}$ where x=1 or 2

Oxidation:

$[L_2Pd^{II}O_2Cl_x]^{-x} \rightarrow [L_2Pd^{II}O_2Cl_x]^{(2-x)} + 2e^-$ $E_{ox}$ = +0.48 V (DMF, Au)
 = +0.48 V (DMF, C)
 = +0.57 V ($CH_2Cl_2$, Au)
 = +0.62 V ($CH_2Cl_2$, C)

Reduction:

$[L_2Pd^{II}O_2Cl_x]^{-x} 2e^- \rightarrow [L_2Pd^1Cl_x]^{(q-x)} + O_2^{-(2-q)}$ where q=0 or 1.

$$E_{red} = -1.68 \text{ V (DMF, Au)}$$
$$= -1.56 \text{ V (DMF, C)}$$
$$= -1.73 \text{ V (CH}_2\text{Cl}_2\text{, Au)}$$
$$= -1.69 \text{ V (CH}_2\text{Cl}_2\text{, C)}.$$

Figure 3:
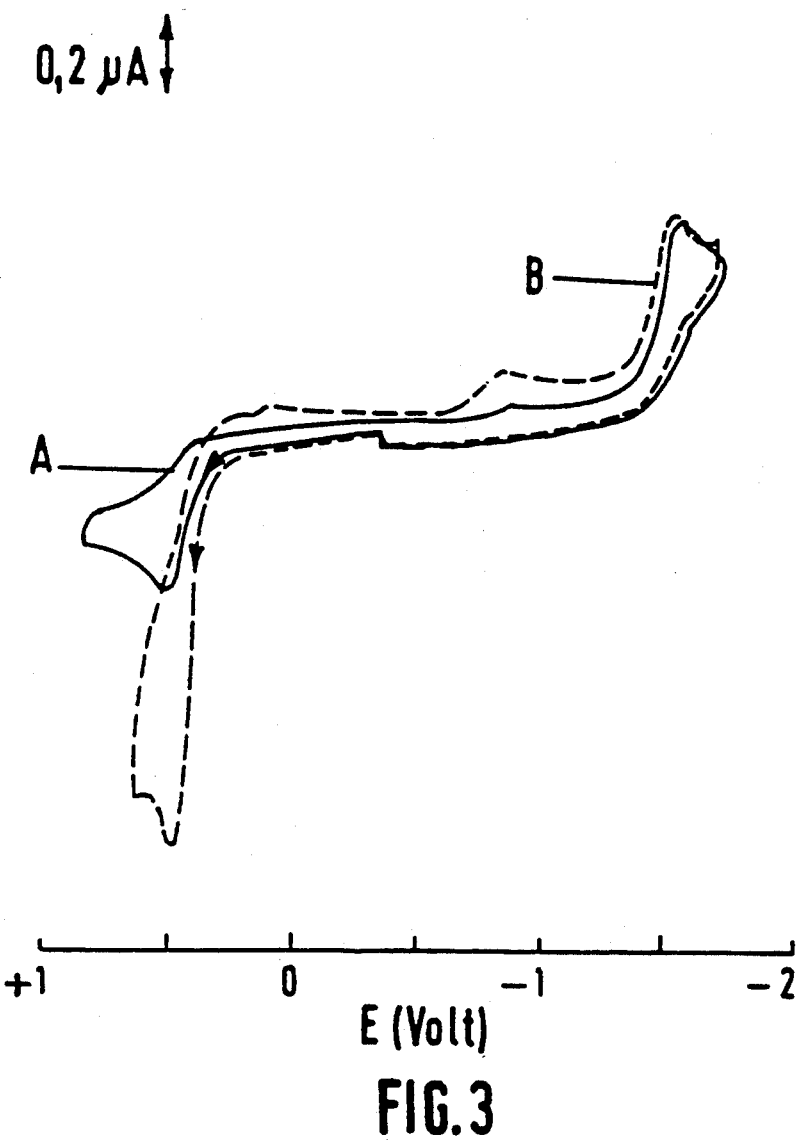

These redox reactions are illustrated on FIG. 1D (voltammograms of $(PPh_3)_4Pd$ under dioxygen atmosphere in the presence of 2 equivalents of chloride ions) and FIGS. 2B and 3B (voltammograms of $(PPh_3)_2PdO_2$ under argon atmosphere in the presence of 2 equivalents of chloride ions). According to these observations, the interaction of the chloride ions with the species in solution proceeds according to the following scheme, where x=1 or 2:

SCHEME IV

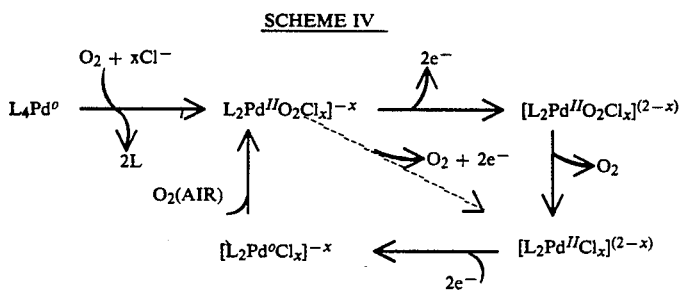

EXAMPLE 3

Electrolysis, Under Controlled Potential, of a Solution of $L_2PdO_2$ (L=PPh$_3$) in the Presence of Chloride Ions A solution of $L_2PdO_2$ is oxidized under argon in $CH_2Cl_2$ in the presence of two equivalents of nBu$_4$NCl in a cell with separated compartments. After the consumption of 1.54 Faraday/mole, a yellow solid is observed that precipitates in the cell while gas evolution is also noticed.

After filtration, the resulting solid (yield: 89% vs the amount of consumed electricity) presents the same physico-chemical characteristics than the complex $L_2PdCl_2$ prepared by chemical means ($^{31}$P. NMR: signal at 23.7 ppm vs $H_3PO_4$ as external reference; IR: $\nu_{Pd-Cl}=350$ cm$^{-1}$).

In consequence:

The oxidation of $L_2Pd_2O_2$ requires two electrons per mole, induces the unloading of molecular oxygen and leads to the complex $L_2PdCl_2$, according to:

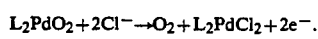

Apart from the observation of gas evolution at the anode, the dioxygen is evidenced in the following manner: a cyclic voltammogram of the solution recorded after electrolysis under argon, in the DMF where $L_2PdCl_2$ is soluble, exhibits a reduction wave attributed to $L_2PdO_2$ around $-1.68$ V while the oxidation wave of $L_2PdO_2$ is not present if the initial scan is anodic.

The reduction of $L_2PdCl_2$ does not lead to the formation of $L_2Pd^0$ but rather to the formation of $L_2Pd^{II}O_2$, indicative of the presence of dioxygen in solution.

EXAMPLE 4

Electrolysis Under Controlled Potential of a Solution of $L_2PdO_2$(L=PPh$_3$) in the Presence of Chloride Ions. Quantitative Evaluation of the Amount of Desorbed Dioxygen The electrolysis of a solution of $L_2PdO_2$ is carried out under the following conditions:

Set-up: cell equipped with a double envelope for the circulation of a fluid for heat-exchange, and with compartments separated by a porous glass; anode made of carbon (RVC 1000, Carbone Lorraine); platinum grid cathode; a Saturated Calomel Electrode (S.C.E.) as a reference electrode; an oxygen analyzer SERVOMEX on line with a volumeter BROOKS for, respectively, the analysis of the $O_2$ purity and the determination of the amount of gas produced.

Medium composition:solvent:dimethylformamide, 70 mL; $L_2PdO_2$ 5 mM; benzyl-tri-n-butyl ammonium chloride 11 mM; supporting electrolyte, tetra-n-butylammonium hexafluorophosphate, 0.3M; medium saturated wiht dioxygen.

Operation Conditions: the temperature of the solution is held at 20° C. by the circulation of water in the double envelope, the applied potential is $+0.8$ V vs. S.C.E.

Results: 7.1 NmL of gas of an average composition of 98.4% in dioxygen, are collected which correspond to the production of 0.31 mmole of $O_2$ (86% of the expected amount). The faradaic yield, calculated versus the amount of dioxygen produced, assuming two electrons per $O_2$ molecule, is of 80.8%.

EXAMPLE 5

Electrochemistry of the Complex $L_2PdO_2$ Prepared in Situ Starting From $PdCl_2$ and the Triphenylphosphine, $PPh_3$ The addition of 2 equivalents of triphenylphosphine, $PPh_3$, on a suspension of $PdCl_2$ in DMF leads quickly to a yellow solution, characteristic of the $(PPh_3)_2PdCl_2$ complex.

The voltammograms (scan rate 200 mV/s, gold electrode) recorded for this complex generated in situ, are identical to the ones recorded for the complex $(PPh_3)_2PdCl_2$ prepared and isolated in the solid state and then dissolved.

A. Electrochemistry in the Absence of Dioxygen Reduction:

$E_{red}$ = −0.97 V (DMF, Au)

= −0.92 V (DMF, C)

Oxidation of $[L_2Pd^0Cl_x]^{-x}$:

$[L_2Pd^0Cl_x]^{-x} + (2-x)Cl^- \rightarrow L_2PdCl_2 + 2e^-$ $E_{ox}$ = +0.015 V (DMF, Au)

= +0.05 V (DMF, C)

B. Electrochemistry in the Presence of Dioxygen

In the presence of dioxygen, the oxidation wave of the electrogenated zero-valent complex, $[(PPh_3)_2Pd^0Cl_x]^{-x}$ at +0.015 V disappears and a new complex arises that is oxidized at more positive potentials, characteristic of $[(PPh_3)_2Pd^{II}O_2Cl_x]^{-x}$.

Reduction of the starting complex:

$(PPh_3)_2Pd^{II}Cl_2 + 2e^- \rightarrow [(PPh_3)_2Pd^0Cl_2]^{-x} + (2-x)Cl^-$ $E_{red}$ = −0.99 (DMF, Au) (same potential than the $O_2$ reduction wave)

Formation of the dioxygenated complex:

$[(PPh_3)_2Pd^0Cl_x]^{-x} + O_2 \rightarrow [(PPh_3)_2Pd^{II}O_2Cl_x]^{-x}$

Reduction of the dioxygenated complex:

$[(PPh_3)_2Pd^{II}O_2Cl_x]^{-x} + 2e^- \rightarrow [(PPh_3)_2Pd^qCl_x]^{(q-x)} + O_2^{-(2-q)}$ where q=0 or 1.

$E_{red}$ = −1.67 V (DMF, Au)

= −1.60 V (DMF, C)

Oxidation of the dioxygenated complex:

$[(PPh_3)_2Pd^{II}O_2Cl_x]^{-x} \rightarrow [(PPh_3)_2PdCl_x]^{2-x} + O_2 + 2e^-$ $E_{ox}$ = +0.43 V (DMF, Au)

= +0.43 V (DMF, C)

Figure 4:
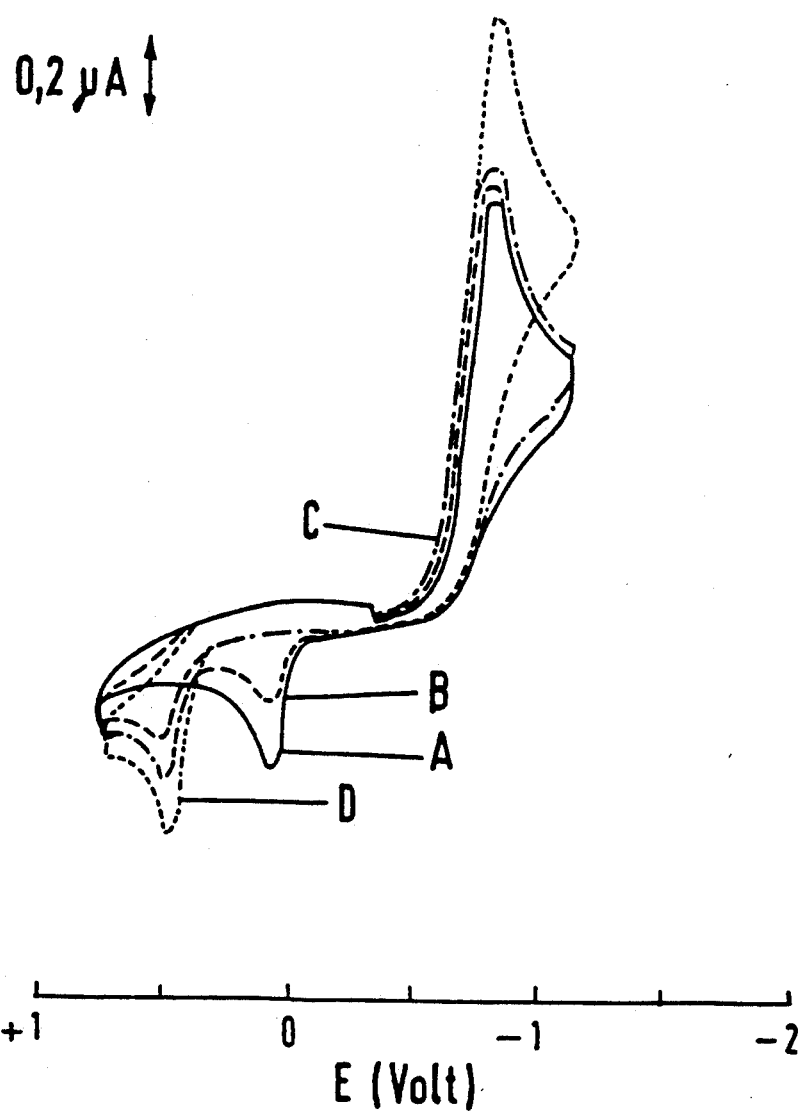

The above results are illustrated on FIG. 4 with the voltammograms of the complex $(PPh_3)_2PdCl_3$ recorded under argon and under $O_2$ atmosphere.

EXAMPLE 6

Electrochemical Study of the Metal Complex $L_2PdCl_2$ in Which the Metal is Coordinated by Two Monodentate Ligands Tri-n-butylphosphine and Two Chloride Ions This study has been performed with solutions of complex at a concentration of 2 mM, using cyclic voltammetry on gold electrode at a scan rate of 200 mV/s in DMF in the presence of 0.3M of $(nBu)_4NBF_4$ as supporting electrolyte. The voltammogram recorded under argon exhibits:

in reduction:

$L_2Pd^{II}Cl_2 + 2e^- \rightarrow [L_2Pd^0Cl_x]^{-x} + (2-x)Cl^-$ $E_{red}$ = −1.39 V a prewave at −0.97 V in oxidation (returning scan):

$[(L_2Pd^0Cl_x]^{-x} + (2-x)Cl^- \rightarrow L_2Pd^{II}Cl_2 + 2e^-$ $E_{ox}$ = −0.40 V The voltammogram recorded under $O_2$ atmosphere exhibits three reduction waves at −0.92, −1.39 and −2.17 V, respectively attributable to the one-electron reduction of dissolved dioxygen into the superoxyde ion $O_2^+$, to the metal-centered reduction of $L_2Pd^{II}Cl_2$ and to the reduction of the dioxygenated complex $[L_2Pd^{II}O_2Cl_x]^{x-}$.

In oxidation, the wave of $]L_2Pd^0Cl_x]^{-x}$ at −0.40 V has disappeared while three new waves have arisen at −0.70, +0.22 and (30 0.60 to +0.80) V, respectively attributable to the oxidation of the superoxyde ion $O_2^+$ into dioxygen, to the oxidation of the dioxygenated complex $[L_2PdO_2Cl_x]^{-x}$ and to the oxidation of the chloride ions $Cl^-$.

More specifically, it is noticeable that the species oxidized at +0.22 V does not result from that reduced at −2.17 V but corresponds to the species resulting from the reaction of dioxygen with $[L_2Pd^0Cl_x]^{-x}$ (reverse of the back scan at −1.5 V or reaction of the superoxyde ion $O_2^-$ with the complex $L_2Pd^{II}Cl_2$, case of the reverse scan at −1.0 V) according to:

$2O_2^- + L_2Pd^{II}Cl_2 \rightarrow [L_2Pd^{II}O_2Cl_x]^{-x} + (2-x)Cl^- + O_2$.

In the case of an excess of chloride ions (addition of $(n-Bu)_4N^+Cl^-$), the same general behavior is observed, but with a slight shift of the oxidation potentials of the species $[L_2Pd^0Cl_x]^{-x}$ and $[L_2PdO_2Cl_x]^{-x}$, respectively from −0.40 to −0.43 V and from +0.22 to +0.19 V. This shift is indicative of a facilitated oxidation for these two species and is due to a stronger interaction of the $Cl^-$ ions with $L_2Pd^0$ and $L_2Pd^{II}O$.

EXAMPLE 7

Electrochemistry of the Complex $L_2PdO_2$ Prepared in Situ Starting From $Na_2PdCl_4$ and Tri-n-butylphosphine, $P(n-Bu)_3$ The operation conditions are the same than the ones described in example 6. Since the starting metal salt, $Na_2PdCl_4$, is soluble in DMF, the addition of two equivalents of tri-n-butylphosphine leads quickly to the formation of the complex $L_2PdCl_2$ (the brown solution turns yellow).

The cyclic voltammetry of this complex, generated in situ in the absence of dioxygen, exhibits in reduction a prewave at −0.97 V and a wave at −1.39 V identical to the one observed for the complex $(n-Bu)_2PdCl_2$.

In oxidation a wave is observed at −0.47 V attributable to the oxidation of $[L_2Pd^0Cl_x]^{-x}$. This potential is 0.07 V more negative than the one measured for $L_2PdCl_2$ without chloride ions in solution (0.40 V), but only 0.04 V more negative than the one measured for the same complex when $(n-Bu)_4N^+Cl^-$ are added (see Example 6). This shift of potentials is thus related to the concentration of $Cl^-$ ions in solution and illustrates the interaction of $Cl^-$ ion with the generated intermediate species.

When dioxygen is present, the voltammogram shows a reduction wave at −0.94 V attributed to the reduction of dioxygen and a second wave at −1.39 V attributed to the reduction of $L_2Pd^{II}Cl_2$. In oxidation the wave attributed to $[L_2Pd^0Cl_x]^{-x}$ has diseappeared while a new one has appeared at $+0.22$ V attributed to $[L_2PdO_2Cl_x]^{-x}$. An oxidation wave at $-0.79$ V corresponds to the oxidation of chloride ions.

Under dioxygen again, if the scan is reversed right after the reduction of dioxygen ($-0.94$ V), an oxidation wave is observed at $+0.22$ V for $[L_2PdO_2Cl_x]^{-x}$ and no wave is present for the oxidation of the zero-valent complex $[L_2Pd^0Cl_x]^{-x}$ at $-0.47$ V. These observations indicate that the dioxygenated complex is formed according to:

$$2O_2^{+-} + L_2Pd^{II}Cl_2 \rightarrow [L_2Pd^{II}O_2Cl_x]^{-x} + (2-x)Cl^- + O_2.$$

What is claimed as desired to be secured by Letters Patent is:

1. A process for separating dioxygen from a gaseous mixture containing dioxygen, which comprises:
   a) absorbing dioxygen by one or more transition metal complexes at a low oxidation state of the formula (A):

$$(L_n(M^{+p})_m(X^{-z})_x)^{mp-xz} \quad (A)$$

wherein L represents a coordinate site which is a part of one or more ligands selected from the group consisting of phosphines, phosphine oxides and phosphites; each of which stabilizes low valences of M;
   wherein M is a transition metal which binds $O_2$ thereby forming a peroxo dihapto deoxygenated species of the formula:

and selected from the group consisting of Pd, Pt, Rh, Ni, Ir and Mo;
   X is a coordinating anion;
   n is an integer of from 2 to 12, and represents the number of coordination sites L,
   p represents the oxidation state number of M in the complex of the formula (A),
   m is an integer of 1 or 2, and represents the number of metal centers of the complex,
   z is an integer of from 1 to 3, and represents the charge of the $X^{-z}$ anion,
   x ranges from 0 to 4, and represents the number of anions X identical or different, coordinated to the metal centers M,
   said absorption causing formation of a peroxo dihapto deoxygenated complex of the formula (B):

$$(L_{n'}(M^{p+2}O_2)_{m'}(X^{-z})_x)^{m'p-x'-z} \quad (B)$$

in which L, M, X, p, z have the same meanings as above,
   n', m', x' have, respectively, the same meanings as n, m and x with $2 \leq n' \leq n,$ $1 \leq m' \leq m,$ and $0 \leq x' \leq x;$ b) desorbing dioxygen from the complex by electrochemically oxidizing the peroxo dihapto product complex (B) obtained by reaction of the complex of formula (A) with $O_2$; and
   c) recovering desorbed oxygen.

2. The process of claim 1, which further comprises, for a continuous process, electrochemically reducing the complex (B) to form regenerated complex (A).

3. The process of claim 1, wherein the metal complex used has the formula (C), $(L_nM^{+p})^{+p}$, in which L, n, M and p have the same meanings as in claim 1.

4. The process of claim 1, wherein the metal M of the metal complex, is coordinated to ligands that possess coordination sites L, and to anions, wherein all coordination sites of M are occupied and the metal complex is of the formula (D):

$$(L_n(M^{+p})(X^{-z})_x)^{p-xz} \quad (D)$$

wherein L, M, X, n, p, x and z are as defined in claim 1.

5. The process of claim 1, wherein the metal complex used is of the formula (E);

$$((L_nM^{+p})_2(X^{-z})^{2p-xz}$$

wherein L, M, X, n, p, z and x are as defined as in claim 1.

6. The process of claim 5, wherein in the complex of the formula: $(L_n(M^{+p})_2(X^{-z})_x)^{2p-xz}$, the structure thereof is maintained with bridging ions $X^{-z}$, or chelating polydentate ligands or both that possess at least two coordination sites L, or a metal/metal bonding or a combination thereof.

7. The process of claim 1, wherein the metal complexes used are anions or cations and are associated to one or several non-coordinative couterions that counterbalance the charge.

8. The process of claim 7, wherein the cations are selected from the group consisting of ammonium quaternary salts, phosphonium quaternary salts, and alkaline or alkaline-earth metals complexed or uncomplexed; and said anions are selected from the group consisting of halides, tetrafluoroborates, hexafluorophosphate, sulfates, carbonates and phosphates.

9. The process of claim 1, wherein the transition metal M is selected from the group consisting of palladium, platinum, nickel, rhodium, iridium and molybdenum.

10. The process of claim 1, wherein said phosphine is selected from the group consisting of mono- or bidentates or both in combination of triphenylphosphines, alkyl-, aryl- and alkylaryl phosphines.

11. The process of claim 1, wherein said phosphine is tri-n-butylphosphine or triphenylphosphine.

12. The process of claim 11, wherein the species (G) is reducible at a potential more negative than the reduction potential of dioxygen to superoxide ion, this superoxide ion being generated in the cathodic compartment and reacted with species (G) to afford the deoxygenated complex (B).

13. The process of claim 1, wherein said phosphine has a hydrophilic group on one of the phosphorus substituents.

14. The process of claim 13, wherein the electrochemical cell is under pressure or where the cathode is a porous gas diffusion electrode.

15. The process of claim 1, wherein compounds (B), (C), (D) and (E) are synthesized before use or are prepared in situ.

16. The process of claim 15, wherein said quaternary salt of ammonium is selected from the group consisting of tetra-n-butyl ammonium tetrafluoroborate and triethylbenzylammonium hexafluorophosphate.

17. The process of claim 15, wherein the solution is made in an organic solvent.

18. The process of claim 17, wherein the organic solvent is selected from the group consisting of dimethylformamide, dimethylsulfoxide, acetonitrile, benzonitile, dichloromethane and tetrahydrofuran.

19. The process of claim 1, wherein the electrochemical oxidation step os performed in an anodic compartment of an electrolysis cell, wherein the electrolytes are selected from the group consisting of perfluoroborate, tetraphenylborate, perfluorophosphate, halide, sulfate, carbonate, phosphate of alkali and alkaline earth metals, and quaternary salts of ammonium and phosphonium.

20. The process of claim 1, wherein the desorption of dioxygen is performed in the anodic compartment of an electrolysis cell, the separation of dioxygen from the solution is effected in a gas-liquid separation tower located after the anodic compartment, and where, for a continuous oxygen separation process, the solution at the outlet of the separation tower is transferred to the cathodic compartment of the electrolysis cell, where the electrochemical reduction is performed at a potential more negative than the one required for oxidation, leading to a complex of a lower oxidation state, which is binds, again, dioxygen in an absorption tower located between the outlet of the cathodic compartment and the inlet of the anodic compartment, the oxidation-reduction cycle then being resumed.

21. The process of claim 1, wherein the absorption of dioxygen is performed by contacting the gas mixture with the metal complex in its reduced form in solution or, aspect, with the active species (A), generated in situ, by mixing a ligand and metal salt in a cathodic compartment which leads to an intermediate species (G) having the formula: $(L_{n''}M+P_{m''}X-{}^t_{x''})^{m''(p+2)-x''z}$ (G)

wherein n'' is an integer of from 2 to 12, and represents the number of coordination sites L;
  m'' is an integer of 1 to 2, and represents the number of metal centers of the complex;
  x'' ranges from 0 to 4, and represents the number of anions X identical or different, coordinated to the metal centers M;
  said species (G) is reduced at a potential to produce (A), the cycle is then resumed.

22. The process of claim 1, wherein the organic solvent exhibits a low ohmic drop.

23. The process of claim 1, wherein the solution is aqueous, and the ligands are water-soluble ligands.

24. The process of claim 1, wherein the dioxygen separation step is performed under atmospheric pressure.

25. The process of claim 1, wherein the dioxygen separation step is performed at a pressure of 1 to 100 bar.

26. The process of claim 25, wherein said dioxygen separation step is performed under a pressure of 1 to 20 bar.

27. The process of claim 1, wherein X is an organic anion.

28. The process of claim 27, wherein the organic anion is a carboxylate ion.

29. The process of claim 1, wherein X is an organic anion.

30. The process of claim 29, wherein the inorganic anion is a halide ion.

31. The process of claim 30, wherein the halide ion is a chloride ion.

32. The process of claim 1, wherein said gaseous mixture containing dioxygen is air.

33. The process of claim 1, wherein said process comprises purifying gaseous mixtures containing dioxygen.

34. The process of claim 1, wherein said gaseous mixture containing dioxygen is air.

35. The process of claim 1, which is used to purify gas mixtures containing dioxygen.

* * * * *